United States Patent [19]

Watson et al.

[11] Patent Number: 4,659,362
[45] Date of Patent: Apr. 21, 1987

[54] HERBICIDAL 5-PYRIMIDYLCYCLOHEXAN-1,3-DIONE DERIVATIVES

[75] Inventors: Keith G. Watson, Box Hill North; Graeme J. Farquharson, Reservoir, both of Australia

[73] Assignee: ICI Australia Limited, Melbourne, Australia

[21] Appl. No.: 525,481

[22] Filed: Aug. 22, 1983

[30] Foreign Application Priority Data

Sep. 2, 1982 [AU] Australia .................................. 5700
May 18, 1983 [AU] Australia .................................. 9406

[51] Int. Cl.⁴ .................. A01N 43/54; C07D 239/26; C07D 239/30; C07D 239/34
[52] U.S. Cl. .................................. 71/92; 544/301; 544/311; 544/316; 544/334; 544/335
[58] Field of Search .................. 71/92; 544/302, 335, 544/301

[56] References Cited

U.S. PATENT DOCUMENTS

| | | | |
|---|---|---|---|
| 3,950,420 | 4/1976 | Sawaki et al. | 71/88 |
| 3,999,974 | 12/1976 | Hirono et al. | 71/92 |
| 4,033,754 | 7/1977 | Sawaki et al. | 71/92 |
| 4,248,618 | 2/1981 | Serban et al. | 71/92 |
| 4,249,937 | 2/1981 | Iwataki et al. | 71/97 |
| 4,328,029 | 5/1982 | Thomas et al. | 71/92 |
| 4,427,437 | 1/1984 | Serban et al. | 71/92 |
| 4,545,806 | 10/1985 | Jahn et al. | 71/88 |

FOREIGN PATENT DOCUMENTS 0066195 5/1982 European Pat. Off. ............ 546/334
1461170 1/1977 United Kingdom .

OTHER PUBLICATIONS

Bredereck et al., *Liebigs Ann. der Chemie*, vol. 766, pp. 73–88, (1972).

*Primary Examiner*—Donald G. Daus
*Assistant Examiner*—Stephen M. Kapner
*Attorney, Agent, or Firm*—Cushman, Darby & Cushman

[57] ABSTRACT

The invention concerns novel compounds of the formula I

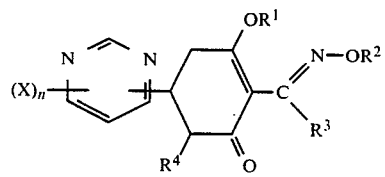

wherein:
X are selected from halogen, nitro, cyano, alkyl, substituted alkyl, hydroxy, alkoxy, substituted alkoxy, alkenyl, alkenyloxy, alkynyl, alkynyloxy, acyloxy, alkoxycarbonyl, alkylthio, alkylsulfinyl, alkylsulfonyl, sulfamoyl, substituted sulfamoyl, alkanoyloxy, benzyloxy, substituted benzyloxy, amino, substituted amino, and the groups formyl and alkanoyl and the oxime, imine and Schiff base derivatives thereof;

$R^1$ is selected from hydrogen, alkyl, alkenyl, alkynyl, substituted alkyl, alkylsulfonyl, arylsulfonyl, acyl and an inorganic or organic cation;

$R^2$ is selected from alkyl, substituted alkyl, alkenyl, haloalkenyl, alkynyl and haloalkynyl;

$R^3$ is selected from alkyl, fluoroalkyl, alkenyl, alkynyl, and phenyl;

$R^4$ is selected from hydrogen, halogen, alkyl, cyano and alkoxycarbonyl; and n is the integer 3.

The compounds of the invention show herbicidal properties and plant growth regulating properties and in further embodiments the invention provides processes for the preparation of compounds of formula I, intermediates useful in the preparation of the compounds of formula I, compositions containing as active ingredient a compound of formula I, and herbicidal and plant growth regulating processes utilizing compounds of formula I.

8 Claims, No Drawings

HERBICIDAL 5-PYRIMIDYLCYCLOHEXAN-1,3-DIONE DERIVATIVES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds and to plant growth regulating compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Patent No. 464 655 and its equivalents such as UK Patent No. 1 461 170 and U.S. Pat. No. 3,950,420.

More recently, at the 1980 British Crop Protection Conference ("1980 British Crop Protection Conference-Weeds, Proceedings Vol 1, Research Reports", pp 39 to 46, British Crop Protection Council, 1980), a new cyclohexane-1,3-dione grass herbicide code named NP 55 (2-(N-ethoxybutrimidoyl)-5-(2-ethylthiopropyl)-3-hydroxy-2-cyclohexen-1-one) was announced. This compound is disclosed in Australian Patent Application No. AU-A1-35,314/78 and its equivalents.

It has now been found that a new group of cyclohexane-1,3-dione derivatives which have a 5-pyrimidyl substituent exhibit particularly useful herbicidal activity.

Accordingly the invention provides a compound of formula I:

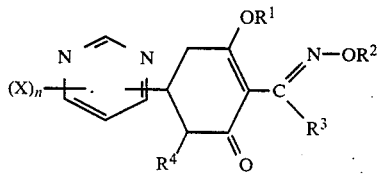

wherein:

X, which may be the same or different, are independently selected from the group consisting of: halogen; nitro; cyano; $C_1$ to $C_6$ alkyl; $C_1$ to $C_6$ alkyl substituted with a substituent selected from the group consisting of halogen, nitro, hydroxy, $C_1$ to $C_6$ alkoxy and $C_1$ to $C_6$ alkylthio; $C_2$ to $C_6$ alkenyl; $C_2$ to $C_6$ alkynyl; hydroxy; $C_1$ to $C_6$ alkoxy; $C_1$ to $C_6$ alkoxy substituted with a substituent selected from halogen and $C_1$ to $C_6$ alkoxy; $C_2$ to $C_6$ alkenyloxy; $C_2$ to $C_6$ alkynyloxy; $C_2$ to $C_6$ alkanoyloxy; ($C_1$ to $C_6$ alkoxy)carbonyl; $C_1$ to $C_6$ alkylthio; $C_1$ to $C_6$ alkylsulfinyl; $C_1$ to $C_6$ alkylsulfonyl; sulfamoyl; N-($C_1$ to $C_6$ alkyl)sulfamoyl; N,N-di($C_1$ to $C_6$ alkyl)-sulfamoyl; benzyloxy; substituted benzyloxy wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl; the group $NR^5R^6$ wherein $R^5$ and $R^6$ are independently selected from the group consisting of hydrogen, $C_1$ to $C_6$ alkyl, $C_2$ to $C_6$ alkanoyl, benzoyl and benzyl; the groups formyl and $C_2$ to $C_6$ alkanoyl and the oxime, imine and Schiff base derivatives thereof;

$R^1$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^2$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio;

$R^3$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl;

$R^4$ is selected from the group consisting of: hydrogen; halogen; cyano; $C_1$ to $C_6$ alkyl; and ($C_1$ to $C_6$ alkoxy)-carbonyl; and n is the integer 3.

When in the compound of formula I X is chosen from the groups formyl and $C_2$ to $C_6$ alkanoyl and the oxime, imine and Schiff base derivatives thereof, the nature of the oxime, imine and Schiff base derivatives is not narrowly critical. Although not intending to be bound by theory, it is believed that in the plant the (substituted) imine group may be removed to give the corresponding compound of formula I in which X is formyl or $C_2$ to $C_6$ alkanoyl. Suitable values for the groups formyl and $C_2$ to $C_6$ alkanoyl and the oxime, imine and Schiff base derivatives thereof include groups of the formula —C($R^7$)=$NR^8$ wherein $R^7$ is chosen from hydrogen and $C_1$ to $C_5$ alkyl, and $R^8$ is chosen from hydrogen, $C_1$ to $C_6$ alkyl, phenyl, benzyl, hydroxy, $C_1$ to $C_6$ alkoxy, phenoxy and benzyloxy.

When in the compound of formula I $R^1$ is chosen from acyl the nature of the acyl group is not narrowly critical. Although not intending to be bound by theory, it is believed that when $R^1$ is acyl the acyl group may be removed in the plant by hydrolysis to give the corresponding compound of formula I in which $R^1$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^1$ is chosen from an inorganic or organic cation the nature of the cation is not narrowly critical. Although not intending to be bound by theory, it is believed that when $R^1$ is a cation the cation may be removed in the plant to give a compound of formula I wherein $R^1$ is hydrogen. Suitable inorganic cations include the alkali and alkaline earth metal ions, heavy metal ions including the transition metal ions, and the ammonium ion. Suitable organic cations include the cation $R^9R^{10}R^{11}R^{12}N^\oplus$ wherein $R^9$, $R^{10}$, $R^{11}$ and $R^{12}$ are independently chosen from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents chosen from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

The compounds of the invention may exist in two isomeric forms as shown, below wherein $\phi$ represents the group

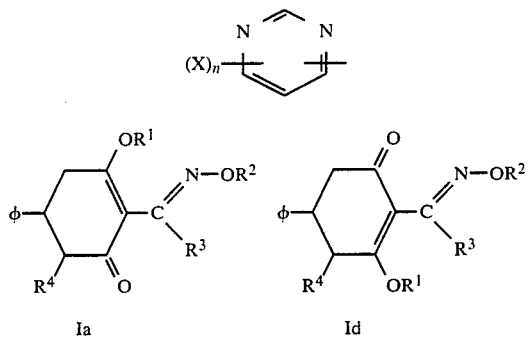

It should be recognized that when $R^1$ is hydrogen, the compounds of the invention may exist in any one of four tautomeric forms as shown below.

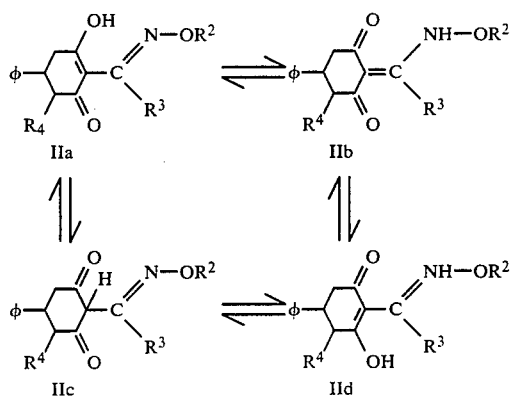

Suitable X include $C_1$ to $C_6$ alkyl, $C_1$ to $C_6$ alkoxy, $C_1$ to $C_6$ alkylthio, halogen, $C_1$ to $C_6$ haloalkyl, amino, $C_1$ to $C_6$ alkylamino and di($C_1$ to $C_6$ alkyl)amino.

Suitable $R^1$ include: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl)sulfonyl; benzenesulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation.

Suitable $R^2$ include: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

Suitable $R^3$ include: $C_1$ to $C_6$ alkyl; $C_1$ to $C_6$ fluoroalkyl; $C_2$ to $C_6$ alkenyl; $C_2$ to $C_6$ alkynyl; and phenyl.

Suitable $R^4$ include hydrogen.

Suitable n is the integer 3.

Preferred compounds of the invention include those compounds of formula I wherein:

X are independently selected from the group consisting of $C_1$ to $C_6$ alkyl, $C_1$ to $C_6$ alkoxy, $C_1$ to $C_6$ alkylthio, $C_1$ to $C_6$ alkylsulfinyl, $C_1$ to $C_6$ alkylsulfonyl, halogen, amino, N-($C_1$ to $C_6$ alkyl)amino and N,N-di($C_1$ to $C_6$ alkyl)amino;

$R^1$ is selected from the group consisting of: hydrogen; $C_2$ to $C_6$ alkanoyl; benzoyl and substituted benzoyl wherein the benzene ring is substituted with from one to three substituents selected from the group consisting of halogen, nitro, $C_1$ to $C_6$ alkyl and $C_1$ to $C_6$ alkoxy; benzenesulfonyl and substituted benzenesulfonyl wherein the benzene ring is substituted with from one to three substituents selected from the group consisting of halogen, nitro, $C_1$ to $C_6$ alkyl and $C_1$ to $C_6$ alkoxy; and an inorganic or an organic cation selected from the alkali metals such as lithium, potassium and sodium, the alkaline earth metals such as magnesium, calcium and barium, the transition metals such as manganese, copper, zinc, iron, nickel, cobalt and silver, the ammonium ion and the tri- and tetra-(alkyl)ammonium ions wherein alkyl is selected from $C_1$ to $C_6$ alkyl and $C_1$ to $C_6$ hydroxyalkyl;

$R^2$ is selected from the group consisting of $C_1$ to $C_6$ alkyl, $C_2$ to $C_6$ alkenyl, $C_2$ to $C_6$ alkynyl, $C_1$ to $C_6$ haloalkyl, $C_2$ to $C_6$ haloalkenyl and $C_2$ to $C_6$ haloalkynyl;

$R^3$ is selected from $C_1$ to $C_6$ alkyl;

$R^4$ is selected from hydrogen and halogen; and n is the integer 3.

More preferred compounds of the invention include those compound of formula I in which the pyrimidine ring is linked through the 5-position to the cyclohexane ring. That is, compounds of formula III:

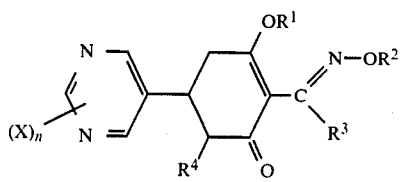

wherein:

X are independently selected from the group consisting of $C_1$ to $C_6$ alkyl, $C_1$ to $C_6$ alkoxy, $C_1$ to $C_6$ alkylthio, $C_1$ to $C_6$ alkylsulfinyl, $C_1$ to $C_6$ alkylsulfonyl, halogen, amino, N-($C_1$ to $C_6$ alkyl)amino and N,N-di($C_1$ to $C_6$ alkyl)amino;

$R^1$ is selected from the group consisting of hydrogen, $C_2$ to $C_6$ alkanoyl, benzoyl, the alkali metals, the transition metals, the ammonium ion and the tri- and tetra-(alkyl)ammonium ions wherein alkyl is selected from $C_1$ to $C_6$ alkyl and $C_1$ to $C_6$ hydroxyalkyl;

$R^2$ is selected from the group consisting of $C_1$ to $C_3$ alkyl, $C_1$ to $C_3$ haloalkyl, allyl and haloallyl;

$R^3$ is selected from $C_1$ to $C_3$ alkyl;

$R^4$ is hydrogen; and n is the integer 3.

Included among the more preferred compounds of the invention are those 5-pyrimidyl compounds which are substituted in the 2-, 4- and 6-positions of the pyrimidine ring. That is, compounds of formula III wherein:

X is independently selected from the group consisting of $C_1$ to $C_6$ alkyl, $C_1$ to $C_6$ alkoxy, $C_1$ to $C_6$ alkylthio and N,N-di($C_1$ to $C_6$ alkyl)amino;

$R^1$ is selected from the group consisting of hydrogen, $C_2$ to $C_6$ alkanoyl and the alkali metals;

$R^2$ is selected from the group consisting of $C_1$ to $C_3$ alkyl, allyl and haloallyl;

$R^3$ is selected from $C_1$ to $C_3$ alkyl;

$R^4$ is hydrogen; and n is the integer 3.

Particularly preferred values for X include methyl, methoxy, methylmercapto and N,N-dimethylamino.

Particularly preferred values for $R^1$ include hydrogen, $C_2$ to $C_6$ alkanoyl, sodium and potassium.

Particularly preferred values for $R^2$ include ethyl, n-propyl, allyl and chloroallyl;

Particularly preferred values for $R^3$ include ethyl and n-propyl.

Examples of compounds embraced by the invention include:

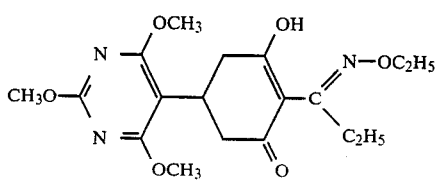

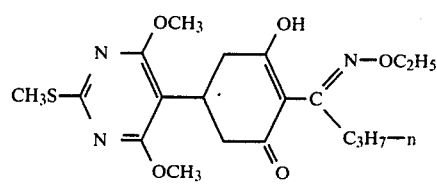

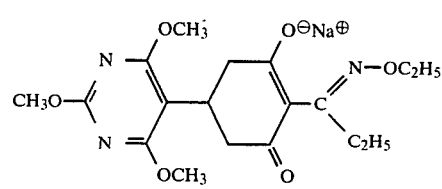

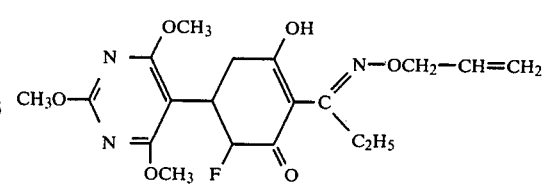

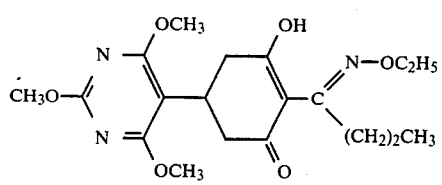

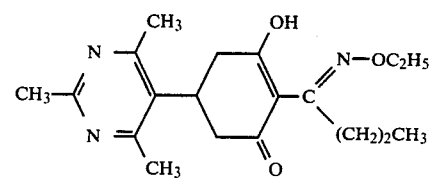

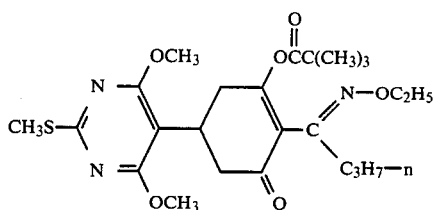

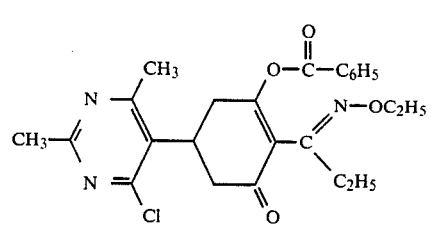

Specific examples of the compounds of the invention include those compounds detailed in Table 1.

TABLE 1

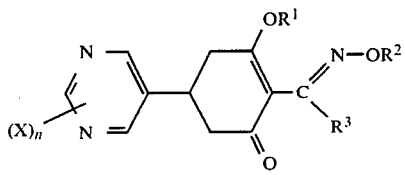

| Compound No | $(X)_n$ | $R^1$ | $R^2$ | $R^3$ |
| --- | --- | --- | --- | --- |
| 1 | 2,4,6-$(CH_3O)_3$ | H | $C_2H_5$ | $C_2H_5$ |
| 2 | 2-$CH_3S$—4,6-$(CH_3O)_2$ | H | $C_2H_5$ | n-$C_3H_7$ |
| 3 | 2,4-$(CH_3O)_2$—6-$(CH_3)_2N$ | H | $C_2H_5$ | n-$C_3H_7$ |
| 4 | 2,4,6-$(CH_3)_3$ | H | $C_2H_5$ | n-$C_3H_7$ |
| 5 | 2,4,6-$(CH_3O)_3$ | H | $C_2H_5$ | n-$C_3H_7$ |
| 6 | 2-$CH_3S$—4,6-$(CH_3O)_2$ | H | $CH_2CH=CHCl$ | $C_2H_5$ |
| 7 | 2-$CH_3S$—4,6-$(CH_3O)_2$ | $COC(CH_3)_3$ | $C_2H_5$ | n-$C_3H_7$ |
| 8 | 2,4,6-$(CH_3O)_3$ | Na | $C_2H_5$ | n-$C_3H_7$ |

The compounds of the invention may be prepared by a variety of methods and in a further aspect the invention provides methods for the preparation of compounds of formula I.

Conveniently the preparation of the compounds of the invention can be considered in three or four parts.

Part A involves the formation of a 5-arylcyclohexan-1,3-dione of formula IX. This reaction may be carried out in a two step process by:

(i) reacting, preferably in the presence of a base, an aldehyde derivative of formula V with acetone (IVa) or an acetone derivative of formula IVb to form a ketone derivative of formula VIa or VIb respectively; and reacting, preferably in the presence of a base, a ketone derivative of formula VIa with a malonic acid ester derivative of formula VIIa or a ketone derivative of formula VIb with a malonic acid ester of formula VIIb, to give an intermediate of formula VIIIa or VIIIb respectively which may be isolated or hydrolysed directly, preferably in the presence of an acid, to give a 5-arylcyclohexan-1,3-dione of formula IX, or reacting, preferably in the presence of a base, a ketone derivative of formula VIa with an alkanoic acid ester of formula VIIc to give a 5-arylcyclohexan-1,3-dione of formula IX;

(ii) reacting, preferably in the presence of a base, an aldehyde derivative of formula V with a malonic acid ester of formula VIIb to give an arylmethylidenemalonate derivative of formula VIc which is in turn reacted, preferably in the presence of a base, with an acetoacetic acid ester derivative of formula VIId to give an intermediate of formula VIIIc which may be isolated or hydrolysed directly, preferably in the presence of an acid, to give a 5-arylcyclohexan-1,3-dione of formula IX; or (iii) reacting, preferably in the presence of a base, an aldehyde derivative of formula V with an acetic acid ester of formula IVc to give a 2-arylalkenoate derivative of formula VId which is in turn reacted, preferably in the presence of a base, with an acetoacetic acid ester derivative of formula VII d to give an intermediate of formula VIIIa which may be isolated or hydrolysed directly, preferably in the presence of an acid, to give a 5-arylcyclohexan-1,3-dione of formula IX.

Part B involves the acylation of a compound of formula IX to give a 2-acyl-5-arylcyclohexan-1,3-dione of formula XIII. This reaction may be carried out by reacting a 5-arylcyclohexan-1,3-dione of formula IX with:

(iv) an acid anhydride of formula X in the presence of either an alkali metal salt of the corresponding acid of formula XI or an alkoxide salt of formula XII, wherein M is an alkali metal ion and R is $C_1$ to $C_6$ alkyl;

(v) an acid anhydride of formula X in the presence of the corresponding acid of formula XIV;

(vi) an acid halide of formula XV, wherein hal represents halogen, in the presence of a Lewis acid catalyst;

(vii) a mixture of an acid halide of formula XV and the corresponding acid of formula XIV; or (viii) with an alkali or alkaline earth metal hydride followed by reaction with an acid anhydride of formula X or an acid halide of formula XV.

Alternatively, this acylation reaction may be carried out by:

(ix) reacting a 5-arylcyclohexan-1,3-dione of formula IX with an acid halide of formula XV in the presence of pyridine to give an intermediate O-acyl derivative of formula XVI; and (x) reacting the intermediate of formula XVI with a Lewis acid catalyst;

(xi) reacting the intermediate of formula XVI with the acid of formula XIV; or (xii) reacting the intermediate of formula XVI with imidazole.

Part C involves the formation of a compound of the invention of formula I wherein $R^1$ is hydrogen, that is a compound of formula II. This reaction may be carried out either by reacting a 2-acyl-5-arylcyclohexan-1,3-dione of formula XIII with:

(xiii) an alkoxyamine derivative of formula XVII; or (xiv) hydroxylamine to give an intermediate oxime derivative of formula XVIII and reacting that intermediate oxide derivative of formula XVIII with an alkylating agent of formula XIX wherein L is a leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Part D involves the formation of a compound of the invention of formula I wherein $R^1$ is a substituent other than hydrogen.

Compounds of the invention of formula I, wherein $R^1$ forms an ether, acyl or sulfonyl derivative of a compound of formula II, may be prepared from the corresponding compounds of the invention of formula II by reacting with an etherification, acylation or sulfonylation reagent of formula XX.

Compounds of the invention of formula I wherein $R^1$ is an inorganic or organic cation may be prepared from the compounds of the invention of formula I wherein $R^1$ is hydrogen, that is, compounds of formula II, by reacting said compounds of formula II with an inorganic or organic salt. For example, the compounds of formula I wherein $R^1$ is an alkali metal ion may be prepared by reacting the appropriate compound of formula II with the appropriate alkali metal hydroxide or alkoxylate. The compounds of formula I wherein $R^1$ is a transition metal ion or an organic cation may similarly be prepared by reacting the appropriate compound of formula II with an appropriate transition metal salt or organic base. Alternatively the compounds of formula I wherein $R^1$ is a transition metal ion or an organic cation may be prepared by reacting the appropriate compound of formula I wherein $R^1$ is an alkali metal ion with an appropriate transition metal salt or organic salt.

Accordingly, in a further aspect the invention provides a process for the preparation of a compound of formula I, as hereinbefore defined, which process comprises:

reacting 2-acyl-5-(aryl)cyclohexane-1,3-dione derivative of formula XIII with an alkoxyamine derivative of formula XVII to give a compound of the invention of formula II or reacting the 2-acyl-5-(aryl)cyclohexane-1,3-dione derivative of formula XIII with hydroxylamine and alkylating the oxime intermediate of formula XVIII with an alkylating agent of formula XIX, wherein L is a leaving group, to give a compound of the invention of formula II; and optionally reacting the compound of the invention of formula II with a compound of formula XX, wherein L is a leaving group, to give a compound of the invention of formula I.

The structures of the compounds described above are detailed on the following pages wherein $\phi$ represents the group

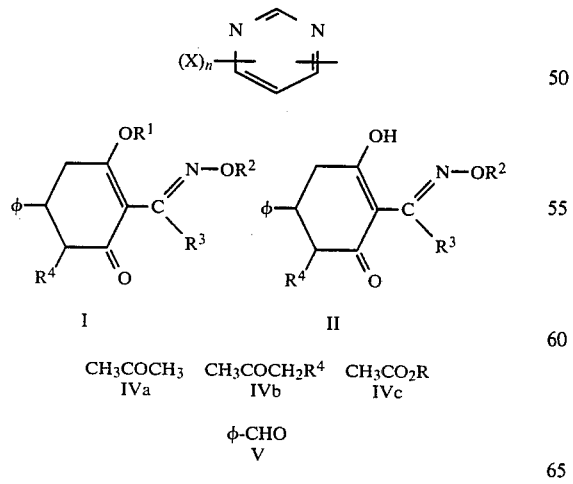

CH$_3$COCH$_3$  CH$_3$COCH$_2$R$^4$  CH$_3$CO$_2$R
IVa            IVb             IVc $\phi$-CHO
V $\phi$-CH=CH—COCH$_3$   $\phi$-CH=CR$^4$—COCH$_3$
VIa                    VIb $\phi$-CH=C(CO$_2$R)$_2$   $\phi$-CH=CH—CO$_2$R
VIc                     VId R$^4$CH(CO$_2$R)$_2$   CH$_2$(CO$_2$R)$_2$
VIIa               VIIb R$^4$CH$_2$CO$_2$R   CH$_3$COCHR$^4$CO$_2$R
VIIc             VIId

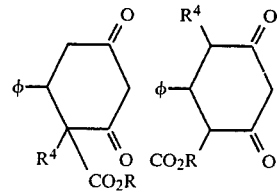

VIIIa        VIIIb

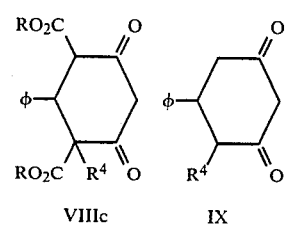

VIIIc         IX (R$^3$CO)$_2$O   R$^3$CO$_2$M   ROM
X              XI          XII

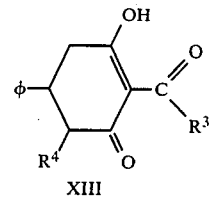

XIII

R$^3$CO$_2$H   R$^3$COhal
XIV        XV

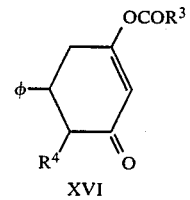

XVI

H$_2$NOR$^2$   R$^2$L   R$^1$L
XVII       XIX    XX

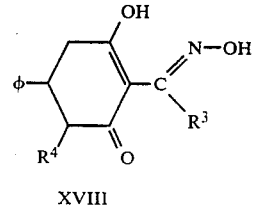

XVIII

Certain of the intermediate compounds of formulae V, VIa, VIb, VIc, VId, VIIIa, VIIIb, VIIIc, IX, XIII, XVI and XVIII are novel compounds are therefore in further embodiments the invention provides novel compounds of formulae V, VIa, VIb, VIc, VId, VIIIa, VIIIb, VIIIc, IX, XIII, XVI and XVIII and processes for the preparation thereof.

For example, only one of the pyrimidinecarboxaldehydes of formula V used in the preparation of the compounds of the invention of formula I, namely, 2,4,6-trimethoxypyrimidine-5-carboxaldehyde, has previously been described.

Accordingly, in a further aspect the invention provides a compound of formula V

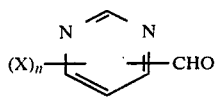     V wherein X and n are as hereinbefore defined provided that X are not all methoxy.

In a further embodiment the invention provides a compound of formula IX

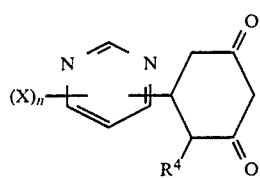     IX wherein X, $R^4$ and n are as hereinbefore defined.

In a still further embodiment the invention provides a compound of formula XIII

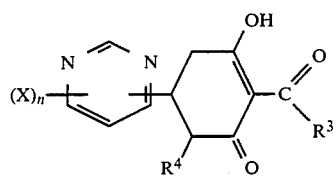     XIII wherein X, $R^3$, $R^4$ and n are as hereinbefore defined.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against moncotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to control monocotyledonous weeds in cultivated crops, especially wild grasses in cereal crops. Certain of such compounds of the invention are especially useful in the control of wild grasses such as wild oats and rye grass in crops of cultivated monocotyledonous plants such as wheat, barley and other varieties of cereals.

Accordingly, in yet a further aspect the invention provides a process for controlling monocotyledonous weeds in cultivated crops, especially wild grasses in cereal crops such as wheat, which process comprises applying to the crop, or to the growth medium of the crop, a compound of formula I, as hereinbefore defined, in an amount sufficient to severely damage or kill the weeds but insufficient to damage the crop substantially.

Surprisingly, it has been found that the 5-(pyrimidyl)-cyclohexan-1,3-dione derivatives of the present invention, that is compounds in which the pyrimidine ring is fully substituted, show high herbicidal activity and/or cereal selective herbicidal activity. In contrast 5-(pyrimidyl)cyclohexan-1,3-dione derivatives in which the pyrimidine ring is unsubstituted or has one or two substituents do not show both high herbicidal activity and cereal selective herbicidal activity and in general are grass herbicides which do not show cereal selective herbicidal activity.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides growth inhibiting, plant damaging, or plant killing compositions comprising a compound of formula I as hereinbefore defined and an agriculturally acceptable carrier therefor.

Certain of the compounds of formula I exhibit useful plant growth regulating activity. For example, while compounds of formula I are selectively active herbicides against wild grasses in crops of cultivated plants at some rates of application they exhibit plant growth regulating effects in said crops.

Plant growth regulating effects may be manifested in a number of ways. For example, suppression of apical dominance, stimulation of auxiliary bud growth stimulation of early flowering and seed formation, enhancement of flowering and increase in seed yield, stem thickening, stem shortening and tillering. Plant growth regulating effects shown in compounds of the invention may include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an agriculturally acceptable carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the performed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier and combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naptha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^1$ is hydrogen are acidic. Therefore, the compounds of formula I may be formulated and applied as the salts of organic or inorganic bases. In formulating an employing the compounds of formula I in the form of their salts either the salts per se, that is the compounds of formula I wherein $R^1$ is an inorganic or an organic cation, may be used in the formulation or the compounds of formula I wherein $R^1$ is hydrogen may be used in the formulation and the salts generated in situ by the use of the appropriate organic or inorganic base.

The mode of application of the compositions of the invention will depend to a large extent on the type of composition used and the facilities available for its application. solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Example of useful complementary herbicides include:
A. benzo-2,1,3-thiadiazin-4-one-2,2-dioxides such as 3-isopropylbenzo-2,1,3-thiadizin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;
E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);
F. phenylurea herbicides such as N'-(3,4-dichlorophenyl)-N,N-dimethylurea (common name diruon) and N,N-dimethyl-N'-[3-(trifluoromethyl)phenyl]urea (common name fluometuron);
G. phenylcarbamoyloxyphenylcarbamates such as 3-[(methoxycarbonyl)amino]phenyl (3-methylphenyl)-carbamate (common name phenmedipham) and 3-[(ethoxycarbonylamino]phenyl phenylcarbamate (common name desmedipham);
H. 2-phenylpyridazin-3-ones such as 5-amino-4-chloro-2-phenylpyridazin-3-one (common name pyrazon);
I. uracil herbicides as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);
J. Triazine herbicides such as 2-chloro-4-ethylamino-6-(isso-propylamino)-1,3,5-triazine (common name atrazine), 2-chloro-4,6-di(ethylamino)-1,3,5-triazine (common name simazine) and 2-azido-4-(isopropylamino)-6-methylthio-1,3,5-triazine (common name aziproptryne);
K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);
L. thiocarbamate herbicides such as S-propyl dipropylthiocarbamate (common name verolate);
M. 1,2,4-triazin-5-one herbicides such as 4-amino-4,5-dihydro-3-methyl-6-phenyl-1,2,4-triazine-5-one (common name metramitron) and 4-amino-6-tert-butyl 4,5-dihydro-3-methylthio-1,3,4-triazin-5one (common name metribuzin);
N. benzoic acid herbicides such as 2,3,6-trichlorobenzoic acid (common name 2,3,6-TBA), 3,6-dichloro-2-methyoxybenzoic acid (common name dicamba) and 3-amino-2,5-dichlorobenzoic acid (common name chloramben);
O. anilide herbicides such as N-butoxymethyl-α-chloro-2',6'-diethylacetanilide (common name butachlor), the corresponding N-methoxy compound (common name alachor), the corresponding N-iso-propyl compound (common name propachlor) and 3',4'-dichloropropionanilide (common name propanil);
P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).

Q. Haloalkanoic herbicides such as 2,2-dichloropropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1-naphthyl)phthalmic acid (common name naptalam) and 3-amino-1,2,4-triazole.

Examples of useful contact herbicides include:

U. bipyridylium herbicides as those in which the active entity is the 1,1'-dimethyl-4,4'-dipyridylium ion (common name paraquat) and those in which the active entity is the 1,1'-ethylene-2,2'-dipryidylium ion (common name diquat);

V. organoarsenical herbicides such as monosodium methanearsonate (common name MSMA); and W. amino acid herbicides such as N-(phosphonomethyl)-glycine (common name glyphosate) and its salts and esters.

The invention is now illustrated by, but in no way limited to, the following Examples.

EXAMPLE 1

2-[1-(Ethoxyimino)propyl]-3-hydroxy-5-(2,4,6-trimethoxy-5-pyrimidyl)cyclohex-2-en-1one (1)

(i) An aqueous solution of 2% sodium hydroxide (15 ml) was added to a stirred suspension of 2,4,6-trimethoxypyrimidine-5-carboxaldehyde (8 g) in acetone (15 ml) and water (15 ml). The mixture was stirred and refluxed for 4 hours, a precipitate slowly forming during this period. The suspension was diluted with water (100 ml) and extracted with chloroform (2×100 ml). The organic layer was washed with water, dried over magnesium sulphate and the solvent was removed by evaporation under reduced pressure to give 1-(2,4,6-trimethoxy-5-pyrimidyl)but-1-en-3-one as a pale yellow solid (8.0 g), mp 98°–99° C.

(ii) Diethylmalonate (4.5 g) was added to a solution of sodium metal (0.65 g) in absolute ethanol (30 ml) and the mixture was heated under reflux with stirring. 1-(2,4,6-Trimethoxy-5-pyrimidylbut-1-en-3-one (6.4 g) was added and the mixture was then boiled under reflux for 2 hours. An aqueous solution of potassium hydroxide (3.5 g in 80 ml of water) was added and the mixture was heated under reflux for a further 5 hours. The solution was cooled and extracted with chloroform (50 ml) and then the aqueous layer was heated to 90° C. and carefully acidified (pH 4.5) with dilute aqueous hydrochloric acid. The resultant precipitate was removed by filtration to give 3-hydroxy-5-(2,4,6-trimethoxy-5-pyrimidyl)cyclohex-2-en-1-one (5.2 g) as a pale yellow crystalline solid, mp 215° C. (dec). Extraction of the filtrate with ethylacetate gave a further 0.7 g of product.

(iii) 3-Hydroxy-5-(2,4,6-trimethoxy-5-pyrimidyl)-cyclohex-2-en-1-one (1.4 g) was dissolved in dimethylformamide (10 ml) at 60° C. and sodium hydride (0.25 g of a 60% dispersion in mineral oil) was added to the solution. The solution was heated to 110° C. and after 15 minutes propionic anhydride (0.7 ml) was added with stirring. The mixture was stirred at 120° C. for a period of 3½ hours and then the solvent was removed under reduced pressure. The residue was partitioned between water (50 ml) and chloroform (2×50 ml) and the organic layer was dried over anhydrous magnesium sulphate and evaporated to give a brown oil. Purification by column chromatography over silica gel (60 g, eluant chloroform) gave 3-hydroxy-5-(2,4,6-trimethoxy-5-pyrimidyl)-2-propionylcyclohex-2-en-1-one (0.9 g, 56%) as a pale yellow oil.

Proton magnetic resonance spectrum (CDCl$_3$; δ in ppm): 1.14 (3H, t); 2.3–4.0 (7H, m); 3.90 (9H, s); 18.10 (1H, s).

(iv) Ethoxyamine hydrochloride (0.30 g) and then aqueous sodium hydroxide (0.15 g in 2 ml of water) were added to a solution of 3-hydroxy-5-(2,4,6-trimethoxy-5-pyrimidyl)-2-propionylcyclohex-2-en-1-one (0.90 g) in absolute ethanol (30 ml) at 20° C. with stirring. After 20 hours at 20° C. the mixture was diluted with water (150 ml) and extracted with chloroform (2×75 ml). The chloroform layer was dried over anhydrous magnesium sulphate and the solvent was removed by evaporation under reduced pressure to give 2-[1-(ethoxyimino)propyl]-3-hydroxy-5-(2,4,6-trimethoxy-5-pyrimidyl)cyclohex-2-en-1-one (900 mg) as a pale yellow oil. The product was characterized by nuclear magnetic resonance spectroscopy.

Proton magnetic resonance spectrum (CDCl$_3$; δ in ppm): 1.18 (3H, t); 1.33 (3H, t); 2.2–4.0 (7H, m); 3.92 (9H, s); 4.10 (2H, q); 15.0 (1H, bs).

EXAMPLE 2

2-[1-(Ethoxyimino)butyl]-3-hydroxy-5-(2,4,6-trimethoxy-5-pyrimidyl)cyclohex-2-en-1-one (5) was prepared from 3-hydroxy-5-(2,4,6-trimethoxy-5-pyrimidyl)cyclohex-2-en-1-one [see Example 1 parts (i) and (ii)], butanoic anhydride and ethoxyamine hydrochloride following essentially the same procedure as that described in Example 1 parts (iii) and (iv). The product was obtained as a nearly colourless oil and was characterized by nuclear magnetic resonance spectroscopy.

Proton magnetic resonance spectrum (CDCl$_3$; δ in ppm): 0.99 (3H, t); 1.31 (3H, t); 1.55 (2H, m); 2.3–4.0 (7H, m); 3.95 (9H, s); 4.10 (2H, q); 14.99 (1H, s).

EXAMPLE 3

2-[1-(Ethoxyimino)butyl]-3-hydroxy-5-(4,6-dimethoxy-2-methylthio-5-pyrimidyl)cyclohex-2-en-1-one (2)

(i) Phosphorus oxychloride (5 ml, 8 g) was added slowly with stirring to a solution of 4,6-dimethoxy-2-methylthiopyrimidine (6.7 g) in dichloroethane (40 ml) and dimethylformamide (10 ml) at room temperature. The solution was boiled under reflux for 3 hours then poured onto ice water and extracted with chloroform (2×60 ml). The chloroform extracts were dried over magnesium sulphate, filtered and evaporated to give 4,6-dimethoxy-2-methylthiopyrimidine-5-carboxaldehyde (7 g, 95%) as a pale yellow solid, mp 136° C.

(ii) 1-(4,6-Dimethoxy-2-methylthio-5-pyrimidyl)but-1-en-3-one was prepared from 4,6-dimethoxy-2-methylthiopyrimidine-5-carboxaldehyde following essentially the same procedure as that described in Example 1 part (i) and was isolated as a pale yellow solid, mp 112° C.

(iii) 3-Hydroxy-5-(4,6-dimethoxy-2-methylthio-5-pyrimidyl)cyclohex-2-en-1-one was prepared from 1-(4,6-dimethoxy-2-methylthio-5-pyrimidyl)but-1-en-3-one following essentially the same procedure as that described in Example 1 part (ii) and was isolated as a cream solid, mp 195°–200° C.

(iv) 2-Butyryl-3-hydroxy-5-[5-(4,6-dimethoxy-2-methylthio)]cyclohex-2-en-1-one was prepared from 3-hydroxy-5-(4,6-dimethoxy-2-methylthio-5-pyrimidyl)cyclohex-2-en-1-one following essentially the same procedure as that described in Example 1 part (iii) and was isolated as an orange oil. Proton magnetic resonance spectrum (CDCl$_3$; $\delta$ in ppm): 0.98 (3H, t); 1.64 (2H, m); 2.52 (3H, s); 2.5–3.7 (7H, m); 3.92 (6H, s); 18.0 (1H, bs).

(v) 2-[1-(Ethoxyimino)butyl]-3-hydroxy-5-(4,6-dimethoxy-2-methylthio-5-pyrimidyl)cyclohex-2-en-1-one was prepared from 2-butyryl-3-hydroxy-5-[5-(4,6-dimethoxy-2-methylthio)]cyclohex-2-en-1-one following essentially the same procedure as that described in Example 1 part (iv) and was isolated as an orange oil. Proton magnetic resonance spectrum (CDCl$_3$ $\delta$ in ppm): 0.98 (3H, t); 1.31 (3H, t); 1.6 (2H, m); 2.52 (3H, s); 2.4–3.8 (7H, m); 3.92 (6H, s); 4.10 (2H, q); 15.0 (1H, bs).

EXAMPLE 4

2-[1-(Ethoxyimino)butyl]-3-hydroxy-5-(2,4-dimethoxy-6-dimethylamino-5-pyrimidyl)cyclohex-2-en-1-one (3)

(i) 2,4-Dimethoxy-6-dimethylaminopyrimidine-5-carboxaldehyde was prepared from 2,4-dimethoxy-6-dimethylaminopyrimidine following essentially the same procedure as that described in Example 3 part (i) and was isolated as a cream solid, mp 150° C.

(ii) 1-(2,4-Dimethoxy-6-dimethylamino-5-pyrimidyl)-but-1-en-3-one was prepared from 2,4-dimethoxy-6-dimethylaminopyrimidine-5-carboxaldehyde following essentially the same procedure as that described in Example 1 part (i) and was isolated as a pale cream-coloured solid, mp 116° C.

(iii) Diethylmalonate (2.8 g, 17 mmole) was added to a solution of sodium (0.40 g, 17 mmole) in ethanol (40 ml) and the solution was heated to reflux temperature. 1-(2,4-Dimethoxy-6-dimethylamino-5-pyrimidyl)but-1-en-3one (2.2 g, 9 mmole) was added and the mixture was boiled under reflux for 2 hours. The ethanol was then distilled off under reduced pressure and dimethylformamide (50 ml) was added and the mixture stirred and heated to 120° C. as n-butyric anhydride (2.9 ml) was added. The solution was heated at 120° C. for 2 hours then the solvent removed under reduced pressure and an aqueous solution of sodium hydroxide was added (100 ml, 4%). The aqueous mixture was refluxed for 4 hours, then cooled and extracted with dichloromethane. The aqueous layer was reheated to 60° C. and neutralized with concentrated hydrochloric acid. Extraction with dichloromethane (2×100 ml) afforded the crude product as a brown oil. Purification by column chromatography over silica gel (eluent dichloromethane) gave 2-butyryl-3-hydroxyl-5-[5-(2,4-dimethoxy-6-dimethylaminopyrimidyl)]cyclohex-2-en-1-one (0.5 g) as a colourless oil. Proton magnetic resonance spectrum (CDCl$_3$; $\delta$ in ppm): 0.98 (3H, t); 1.6 (2H, m); 2.2–3.8 (7H, m); 3.09 (6H, s); 3.84 (6H, s); 18.20 (1H, s).

(iv) 2-[1-(Ethoxyimino)butyl]-3-hydroxy-5-(2,4-dimethoxy-6-dimethylamino-5-pyrimidyl)cyclohex-2-en-1-one was prepared from 2-butyryl-3-hydroxy-5-[5-(2,4-dimethoxy-6-dimethylaminopyrimidyl)]-cyclohex-2-en-1-one following essentially the same procedure as that described in Example 1 part (iv) and was isolated as a brown oil. Proton magnetic resonance spectrum (CDCl$_3$; $\delta$ in ppm): 0.98 (3H, t); 1.31 (3H, t); 1.6 (2H, m); 2.4–4.2 (9H, m); 3.13 (6H, s); 3.88 (6H, s); 10.9 (1H, bs).

EXAMPLE 5

2[1-(Ethoxyimino)butyl]-3-hydroxy-5-[5-(2,4,6-trimethylpyrimidyl)]cyclohex-2-en-1-one (4)

(i) (a) Ethyl 2,4,6-trimethylpyrimidine-5-carboxylate [11.0 g; prepared according to Urban & Shnider, *Helv. Chim Acta,* 41, 1806 (1958)] was stirred with a slight excess of lithium aluminium hydride in dry tetrahydrofuran (100 ml) at room temperature for 2 hr. The solvent was evaporated and the residue was shaken with a little water. The dried (MgSO$_4$) ethyl acetate extract was evaporated and the residue was purified by column chromotography over alumina with ethyl acetate elution to give 5-(hydroxymethyl)-2,4,6-trimethylpyrimidine as white crystals, mp 68° C.

(b) 5-Hydroxymethyl)-2,4,6-trimethylpyrimidine (5.0 g) and manganese dioxide (35 g) were heated at reflux in chloroform (200 ml) with vigorous stirring for 8 hr. The mixture was filtered and the filtrate was evaporated. The residue was chromatographed through a short alumina column with dichloromethane elution to give 2,4,6-trimethylpyrimidine-5-carboxaldehyde as white crystals melting at ambient temperatures. Pmr spectrum (CDCl$_3$; $\delta$ in ppm): 2.71 (3H, s); 2.78 (6H, s); 10.65 (1H, s).

(c) 2,4,6-Trimethylpyrimidine-5-carboxaldehyde (1.4 g) and 1-triphenylphosphoranylidene-2-propane (1.1 equiv) were heated at reflux in toluene (150 ml) for 12 hr. The solvent was evaporated and the residue was purified by column chromatography over xilica gel with ethyl acetate elution to give 1-(2,4,6-trimethylpyrimidin-5-yl)but-1-en-3-one as an oil. Pmr spectrum (CDCl$_3$ $\delta$ in ppm): 2.41 (3H, s); 2.52 (6H, s); 2.68 (3H, s); 6.44 (1H, d); 7.62 (1H, d).

(ii) and (iii) 1-(2,4,6-Trimethylpyrimidin-5-yl)but-1-en-3-one (1.5 g) and sodium diethyl malonate (2.5 equiv) were heated at reflux in absolute ethanol (40 ml) for 13 hr. A dilute aqueous potassium hydroxide solution (4 equiv) was added and the mixture was heated allowing the ethanol to distill off over 4 hr. The hot solution was made just acid by slow addition of a dilute hydrochloric acid solution. Potassium bicarbonate (2equiv) was added and the solvent was evaporated by reduced pressure distillation. The solid residue was thoroughly dried (100° C.; 0.1 mmHg). The residue was extracted with hot anhydrous dimethylformamide (40 ml). The soluble fraction was heated at 100° C. under nitrogen with butyric anhydride (3 ml) for 2 hr. The dimethylformamide (40 ml) was evaporated by reduced pressure distillation and the residue was shaken with a little dilute acetic acid. The whole mixture was extracted into ethyl acetate. The dried (MgSO$_4$) solvent was evaporated and the residue was purified by column chromatography over silica gel with ethyl acetate elution to give 3-hydroxy-5-(2,4,6-trimethylpyrimidin-5-yl)-2-butyrylcyclohex-2-en-1-one as an oil. Pmr spectrum (CDCl$_3$; $\delta$ in ppm): 1.01 (3H, t); 1.69 (2H, m); 2.3–3.9 (7H, m); 2.57 (6H, s); 2.63 (3H, s); 18.33 (1H, s).

(iv) 3-Hydroxy-5-(2,4,6-trimethylpyrimidin-5-yl)-2-butyrylcyclohex-2-en-1-one (0.29 g) was stirred with O-ethylhydroxylamine hydrochloride (0.1 g) and sodium acetate trihydrate (0.14 g) in ethanol (30 ml) at room temperature for 15 hr. The mixture was poured into a saturated aqueous salt solution (50 ml), which was subsequently extracted with ethyl acetate. The dried (Na$_2$SO$_4$) organic extract was evaporated to give 2-[1-(ethoxyimino)butyl]-3-hydroxy-5-(2,4,6-trimethyl-pyrimidin-5-yl)cyclohex-2-en-1-one as a colourless oil. Pmr spectrum (CDCl$_3$; δ in ppm): 1.01 (3H, t); 1.34 (3H, t); ca 1.64 (2H, m); ca 2.3-3.8 (7H, m); 2.59 (6H, s); 2.63 (3H, s); 4.13 (2H, q); 10.66 (1H,s).

EXAMPLE 6

2-[1-(3-Chloroallyloxyimino)butyl]-3-hydroxy-5-(4,6-dimethoxy-2-methylthio-5-pyrimidyl)cyclohex-2-en-1-one (6) was prepared from 2-butyryl-3-hydroxy-5-[5-(4,6-dimethoxy-2-methylthiopyrimidyl)]cyclohex-2-en-1-one (see Example 3) and 3-chloroallyloxyamine hydrochloride following essentially the same procedure as that described in Example 1, part (iv). The product was obtained as a nearly colourless oil and was characterized by nuclear resonance spectroscopy.

Proton magnetic resonance spectrum (CDCl$_3$; δ in ppm): 0.97 (3H, t); 1.6 (2H, m); 2.5-4.0 (7H, m); 2.53 (3H, s); 3.95 (6H, s); 4.4-4.8 (2H, dofd); 5.9-6.4 (2H, m); 15.0 (1H, bs).

EXAMPLE 7

3-Trimethylacetyloxy-2-[1-(ethoxyimino)butyl]-5-(4,6-dimethoxy-2-methylthio-5-pyrimidyl)cyclohex-2-en-1-one (7)

A solution of 3-picoline (40 mg) and 2-[1-ethoxyimino)butyl]-5-(4,6-dimethoxy-2-methylthio-5-pyrimidyl)cyclohex-2-en-1-one (2) (80 mg) in dichloromethane (10 ml) was treated with trimethylacetyl chloride with stirring at room temperature. After 2 hours the solution was washed with dilute hydrochloric acid (1M, 20 ml), separated, dried over anhydrous magnesium sulphate and evaporated under reduced pressure to give 3-trimethylacetyloxy-2-[1-(ethoxyimino)butyl]-5-(4,6-dimethoxy-2-methylthio-5-pyrimidyl)cyclohex-2-en-1-one (7) as a pale brown oil (100 mg) which was characterized by nuclear magnetic resonance spectroscopy.

Proton magnetic resonance spectrum (CDCl$_3$; δ in ppm): 0.99 (3H, t); 1.27 (9H, s); 1.32 (3H, t); 1.6 (2H, m); 2.4-3.8 (7H, m); 2.53 (3H, s); 3.95 (6H, s); 4.12 (2H, q).

EXAMPLE 8

Sodium salt of 2-[1-(ethoxyimino)butyl]-3-hydroxy-5-(2,4,6-trimethoxy-5-pyrimidyl)cyclohex-2-en-1-one (8)

A solution of sodium hydroxide (10 mg) in methanol (10 ml) was added to a solution of 2-[1-(ethoxyimino)-butyl]-3-hydroxy-5-(2,4,6-trimethoxy-5-pyrimidyl)cyclohex-2-en-1-one (5) (60 mg) in methanol (20 ml). The solvent was removed under reduced pressure to give the title compound as a pale brown solid (60 mg), mp >200° C.

EXAMPLE 9

This non-limiting Example illustrates the preparation of formulations of the compounds of the invention.
(a) Emulsifiable Concentrate Compound No 1 was dissolved in toluene containing 7% v/v "Teric" N13 and 3% v/v "Kemmat" SC15B to given an emulsifiable concentrate which may be diluted with water to the required concentration to given an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)
(b) Aqueous Suspension Compound No 1 (5 parts by weight) and "Dyapol" PT (1 part by weight) were added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)
(c) Emulsifiable Concentrate Compound No 1 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to given an aqueous emulsion which may be applied by spraying. ("Solvesso" is a Trade Mark and "Solvesso" 150 is a high boiling point aromatic petroleum fraction.)
(d) Dispersible Powder Compound No 1 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde concensate; "Aerosol" is a Trade Mark and "Aerosol" OT/B is a formulation of the dioctyl ester of sodium sulfosuccinic acid.)
(e) High Strength Concentrate Compound No 1 (99 parts by weight), silica aerogel (0.5 parts by weight) and synthetic amorphous silica (0.5 parts by weight) were blended and ground in a hammer-mill to produce a powder having a particle size less than 200 microns
(f) Dusting Powder Compound No 1 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 10 and 11, in the evaluation of the pre-emergence and post-emergence herbicidal activity of the compounds.

EXAMPLE 10

The pre-emergent herbicidal activity of the compounds of the invention formulated as described in Example 9 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glass house and the effect of the treatment was visually assessed. The results are presented in Table 2 where the damage to plants is rated on a scale of form 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 2

PRE-EMERGENCE HERBICIDAL ACTIVITY

| Compound No | APPLICATION Rate (kg/ha) | TEST PLANT | | | | | | | |
|---|---|---|---|---|---|---|---|---|---|
| | | Wh | Ot | Rg | Jm | P | Ip | Ms | Sf |
| 2 | 1.0 | 4 | 5 | 5 | 5 | 0 | 0 | 0 | 0 |

EXAMPLE 11

The post-emergent herbicidal activity of the compounds of the invention formulated as described in Example 9 was assessed by the following procedure.

The seeds of the test species were sown in rows 2 cm deep in soil contained in seed boxes. The monocotyledonous plants and the dicotyledonous plants were sown in separate seed boxes in duplicante. The four seed boxes were placed in a glass house, lightly watered with an overhead spray to initiate germination and then sub-irrigated as required for optimum plant growth. After the plants had grown to a height of about 10 to 12.5 cm one box of each of the monocotyledonous plants and dicotyledonous plants was removed from the glass house and sprayed with the required quantity of a composition of the invention. After spraying the boxes were returned to the glass house for a further 3 weeks and the effect of treatment was visually assessed by comparison with the untreated contols. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:
Wh: Wheat
Ot: Wild Oats
Rg: Ryegrass
Jm: Japanese millet
P: Peas
Ip: Ipomea
Ms: Mustard
Sf: Sunflower

TABLE 3

POST-EMERGENCE HERBICIDAL ACTIVITY

| Compound No | APPLICATION Rate (kg/ha) | TEST PLANT | | | | | | | |
|---|---|---|---|---|---|---|---|---|---|
| | | Wh | Ot | Rg | Jm | P | Ip | Ms | Sf |
| 1 | 1.0 | 0 | 5 | 5 | 5 | 0 | 0 | 0 | 0 |
| 1 | 0.5 | 0 | 3 | 5 | 5 | 0 | 0 | 0 | 0 |
| 2 | 0.25 | 2 | 5 | 5 | 5 | 0 | 0 | 0 | 0 |
| 2 | 0.06 | 0 | 5 | 2 | 0 | 0 | 0 | 0 | 0 |
| 3 | 1.0 | 3 | 4 | 5 | 5 | 0 | 0 | 0 | 0 |
| 3 | 0.25 | 0 | 1 | 4 | 3 | 0 | 0 | 0 | 0 |
| 4 | 0.1 | 5 | 5 | 5 | — | — | — | — | — |
| 4 | 0.05 | 4 | 5 | 5 | — | — | — | — | — |
| 4 | 0.025 | — | 5 | 4 | — | — | — | — | — |

EXAMPLE 12

The compounds were formulated for test by mixing a appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 4 below. Damage to test plants was assessed after 14 days on a scale of 0 to 5 where 0 is 0 to 20% damage an 5 is is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 4 below. A dash (-) means that no experiment was carried out.

The names of the test plants were as follows:
Sb: Sugar beet
Rp: Rape
Ct: Cotton
Sy: Soy bean
Mz: Maize
Ww: Winter wheat
Rc: Rice
Sn: *Senecio vulgaris*
Ip: *Ipomea purpurea*
Am: *Amaranthus retroflexus*
Pi: *Polygonum aviculare*
Ca: *Chenopodium album*
Ga: *Galium aparine*
Xa: *Xanthium pensylvanicum*
Ab: *Abutilon theophrasti*
Co: *Cassia obtusifolia*
Av: *Avena fatua*
Dg: *Digitaria sanguinalis*
Al: *Alopecurus myosuroides*
St: *Setaria viridis*
Ec: *Echinochloa crus-galli*
Sh: *Sorghum halepense*
Ag: *Agropyron repens*
Cn: *Cyperus rotundas*

TABLE 4

| Compound No | APPLICATION Method | Rate (kg/ha) | Sb | Rp | Ct | Sy | Mz | Ww | Rc | Sn | Ip | Am | Pi | Ca | Ga | Xa | Ab | Co | Av | Dg | Al | St | Ec | Sh | Ag | Cn |
|---|---|---|---|---|---|---|---|---|---|---|---|---|---|---|---|---|---|---|---|---|---|---|---|---|---|---|
| 1 | PRE | 2.0 | — | — | — | — | 5 | 3 | 5 | — | — | — | — | — | — | — | — | — | 5 | 4 | 5 | 5 | 5 | 4 | 5 | — |
| 1 | PRE | 0.4 | — | — | — | — | 3 | 2 | 3 | — | — | — | — | — | — | — | — | — | 3 | 3 | 4 | 5 | 5 | 2 | 2 | — |
| 1 | POST | 2.0 | — | — | — | — | 5 | 4 | 4 | — | — | — | — | — | — | — | — | — | 4 | 4 | 4 | 5 | 5 | 5 | 4 | — |
| 1 | POST | 0.4 | — | — | — | — | 4 | 3 | 4 | — | — | — | — | — | — | — | — | — | 4 | 2 | 3 | 4 | 4 | 4 | 3 | — |
| 2 | PRE | 0.05 | — | — | — | — | 0 | 0 | 2 | — | — | — | — | — | — | — | — | — | 3 | 2 | 0 | 0 | 2 | — | 0 | — |
| 2 | POST | 0.05 | — | — | — | — | 3 | 2 | 0 | — | — | — | — | — | — | — | — | — | 4 | 5 | 2 | 4 | — | 4 | 2 | — |
| 4 | POST | 0.1 | — | — | — | — | 4 | 4 | 3 | — | — | — | — | — | — | — | — | — | 4 | 5 | 4 | 5 | 5 | 5 | 4 | — |
| 4 | POST | 0.02 | — | — | — | — | 3 | 3 | 2 | — | — | — | — | — | — | — | — | — | 4 | 4 | 4 | 4 | 4 | 4 | 0 | — |
| 5 | PRE | 0.4 | — | — | — | — | 1 | 0 | 2 | — | — | — | — | — | — | — | — | — | 3 | 4 | 4 | 4 | 4 | 4 | 1 | — |
| 5 | POST | 0.4 | — | — | — | — | 3 | 0 | 0 | — | — | — | — | — | — | — | — | — | 2 | 3 | 0 | 4 | 2 | 4 | 0 | — |

We claim:

1. A compound of the formula:

wherein:

X are independently selected from the group consisting of $C_1$ to $C_6$ alkyl and $C_1$ to $C_6$ alkoxy;

$R^1$ is selected from the group consisting of hydrogen and the alkali metals;

$R^2$ is selected from the group consisting of $C_1$ to $C_3$ alkyl, allyl and propargyl;

$R^3$ is selected from $C_1$ to $C_3$ alkyl;

$R^4$ is hydrogen; and n is the integer 3.

2. A compound according to claim 1 wherein:

X is methyl or methoxy;

$R^1$ is hydrogen or sodium;

$R^2$ is selected from the group consisting of ethyl, n-propyl, allyl and propargyl;

$R^3$ is ethyl or n-propyl; and n is the integer 3.

3. A compound according to claim 2 selected from the group consisting of:

2-[1-(ethoxyimino)propyl]-3-hydroxy-5-[5-(2,4,6-trimethoxypyrimidyl)]cyclohex-2-en-1-one; and 2-[1-(ethoxyimino)butyl]-3-hydroxy-5-[5-(2,4,6-trimethoxypyrimidyl)]cyclohex-2-en-1-one.

4. A herbicidal composition comprising as active ingredient a compound as defined according to claim 1 and a carrier therefor.

5. A process for severely damaging or killing unwanted monocolyledonous plants which process comprises applying to said plants, an effective amount of a compound as defined according to claim 2.

6. A process for selectively controlling the growth of monocotyledonous weeds in dicotyledonous crops which process comprises applying to said crop, a compound as defined according to claim 1 in an amount sufficient to severely damage or kill said weeds but insufficient to substantially damage said crop.

7. A process for selectively controlling the growth of monocotyledonous weeds in cultivated crops which process comprises applying to said crop a compound as defined according to claim 1 in an amount sufficient to severely damage or kill said weeds but insufficient to substantially damage said crop.

8. A process according to claim 6 or 7 wherein the compound is applied at a rate in the range of from 0.005 to 20 kilograms per hectare.

* * * * *